US010162021B2

(12) United States Patent
Kawabata et al.

(10) Patent No.: US 10,162,021 B2
(45) Date of Patent: Dec. 25, 2018

(54) MAGNETIC FIELD MEASUREMENT DEVICE

(71) Applicant: Hitachi, Ltd., Tokyo (JP)

(72) Inventors: Ryuzo Kawabata, Tokyo (JP); Akihiko Kandori, Tokyo (JP); Taro Osabe, Tokyo (JP); Seiichi Suzuki, Tokyo (JP); Yuudai Kamada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 349 days.

(21) Appl. No.: 14/905,132

(22) PCT Filed: Aug. 2, 2013

(86) PCT No.: PCT/JP2013/070958
§ 371 (c)(1),
(2) Date: Jan. 14, 2016

(87) PCT Pub. No.: WO2015/015628
PCT Pub. Date: Feb. 5, 2015

(65) Prior Publication Data
US 2016/0146909 A1    May 26, 2016

(51) Int. Cl.
*G01R 33/26* (2006.01)
*G01N 24/00* (2006.01)
*H01S 3/091* (2006.01)

(52) U.S. Cl.
CPC ........... *G01R 33/26* (2013.01); *G01N 24/006* (2013.01); *H01S 3/091* (2013.01)

(58) Field of Classification Search
CPC ........ G01R 33/26; G01N 24/006; H01S 3/091
(Continued)

(56) References Cited

U.S. PATENT DOCUMENTS 3,596,201 A * 7/1971 Chester ................. H01S 3/1396
144/34.5
3,649,930 A * 3/1972 Le Floch ............... H01S 3/1398
372/32
(Continued)

FOREIGN PATENT DOCUMENTS

JP          5-50758 U      7/1993
JP       2002-314187 A    10/2002
(Continued)

OTHER PUBLICATIONS

International Search Report of PCT/JP2013/070958.

*Primary Examiner* — Jermele M Hollington
*Assistant Examiner* — Sean Curtis
(74) *Attorney, Agent, or Firm* — Mattingly & Malur, PC

(57) ABSTRACT

A magnetic measurement device has a magnetic sensor including a glass cell having alkali metal gas encapsulated therein that is configured to detect a magnetic field using a magneto-optical characteristic of spin-polarized alkali metal. A laser light source is configured to generate pump light introduced into the magnetic sensor and a coil provided in the same magnetically shielded space as the magnetic sensor is configured to apply a static magnetic field and a RF magnetic field to the magnetic sensor. A signal processor is configured to perform lock-in detection of a light detection signal transmitted through the glass cell of the magnetic sensor, control an intensity of the static magnetic field and a frequency of the RF magnetic field generated by the coil according to a lock-in detection output, and obtain a measurement signal reflecting a magnetic field intensity of an object to be measured in the magnetically shielded space.

6 Claims, 8 Drawing Sheets

(58) Field of Classification Search
USPC .......................................................... 324/304
See application file for complete search history.

(56) References Cited

U.S. PATENT DOCUMENTS

| | | | | |
|---|---|---|---|---|
| 3,667,066 A * | 5/1972 | Kastler | ............... | G04F 5/14 |
| | | | | 331/3 |
| 3,668,547 A * | 6/1972 | Bodlaj | ............... | H01S 3/1398 |
| | | | | 372/32 |
| 3,829,838 A * | 8/1974 | Lewis | ............... | G02B 27/2271 |
| | | | | 345/419 |
| 3,831,108 A * | 8/1974 | Le Floch | ............... | H01S 3/1398 |
| | | | | 372/31 |
| 3,976,957 A * | 8/1976 | Le Floch | ............... | G02F 1/092 |
| | | | | 372/19 |
| 4,539,521 A * | 9/1985 | Matsumoto | ............... | G01R 33/0322 |
| | | | | 250/225 |
| 4,779,279 A * | 10/1988 | Brown | ............... | H01S 3/134 |
| | | | | 372/20 |
| 5,036,278 A * | 7/1991 | Slocum | ............... | G01R 33/26 |
| | | | | 324/304 |
| 5,706,079 A * | 1/1998 | Kersey | ............... | G01D 5/35316 |
| | | | | 356/482 |
| 6,472,869 B1 * | 10/2002 | Upschulte | ............... | G01R 33/26 |
| | | | | 324/300 |
| 6,556,516 B1 * | 4/2003 | Shimazaki | ............... | G11B 11/10595 |
| | | | | 369/116 |
| 6,693,854 B2 * | 2/2004 | Shimazaki | ............... | G11B 11/10595 |
| | | | | 369/13.05 |
| 6,888,780 B2 * | 5/2005 | Happer | ............... | G04F 5/14 |
| | | | | 324/301 |
| 6,891,623 B1 * | 5/2005 | Baudon | ............... | B82Y 10/00 |
| | | | | 356/450 |
| 7,038,450 B2 * | 5/2006 | Romalis | ............... | G01R 33/02 |
| | | | | 324/301 |
| 7,652,473 B2 * | 1/2010 | Kawabata | ............... | G01R 33/032 |
| | | | | 324/301 |
| 7,656,154 B2 * | 2/2010 | Kawabata | ............... | G01R 33/0354 |
| | | | | 324/244.1 |
| 7,902,927 B2 * | 3/2011 | Davis | ............... | H03L 7/26 |
| | | | | 331/176 |
| 7,922,337 B2 * | 4/2011 | Glent-Madsen | ............... | G02B 26/04 |
| | | | | 250/205 |
| 8,264,693 B2 * | 9/2012 | Stoica | ............... | G01R 33/1284 |
| | | | | 356/502 |
| 8,362,768 B2 * | 1/2013 | Nagasaka | ............... | G01N 24/006 |
| | | | | 324/300 |
| 8,405,389 B2 * | 3/2013 | Sugioka | ............... | G01R 33/022 |
| | | | | 324/244.1 |
| 8,957,677 B2 * | 2/2015 | Nagasaka | ............... | G01R 33/0322 |
| | | | | 324/244 |
| 9,229,073 B2 * | 1/2016 | Walker | ............... | G01R 33/26 |
| 9,274,182 B2 * | 3/2016 | Ueno | ............... | G01R 33/032 |
| 9,310,447 B2 * | 4/2016 | Kamada | ............... | G01R 33/26 |
| 9,351,651 B2 * | 5/2016 | Nagasaka | ............... | A61B 5/04008 |
| 9,366,735 B2 * | 6/2016 | Kawabata | ............... | G01R 33/26 |
| 9,720,058 B2 * | 8/2017 | Ueno | ............... | G01R 33/032 |
| 9,726,494 B2 * | 8/2017 | Bulatowicz | ............... | G01R 33/26 |
| 9,810,756 B2 * | 11/2017 | Cochrane | ............... | G01R 33/385 |
| 9,829,544 B2 * | 11/2017 | Bulatowicz | ............... | G01R 33/032 |
| 9,869,731 B1 * | 1/2018 | Hovde | ............... | G01R 33/26 |
| 2002/0018404 A1 * | 2/2002 | Awano | ............... | G11B 11/1051 |
| | | | | 369/13.07 |
| 2002/0175767 A1 * | 11/2002 | Kitching | ............... | G04F 5/14 |
| | | | | 331/3 |
| 2003/0107956 A1 * | 6/2003 | Awano | ............... | G11B 11/1051 |
| | | | | 369/13.43 |
| 2004/0202050 A1 * | 10/2004 | Happer | ............... | G04F 5/14 |
| | | | | 368/10 |
| 2005/0041704 A1 | 2/2005 | Fukuda et al. | | |
| 2007/0120563 A1 * | 5/2007 | Kawabata | ............... | G01R 33/0354 |
| | | | | 324/244.1 |
| 2007/0247241 A1 * | 10/2007 | Braun | ............... | G04F 5/14 |
| | | | | 331/94.1 |
| 2007/0297175 A1 * | 12/2007 | Glent-Madsen | ............... | G02B 26/04 |
| | | | | 362/282 |
| 2009/0091812 A1 * | 4/2009 | Goto | ............... | B82Y 10/00 |
| | | | | 359/107 |
| 2010/0026394 A1 * | 2/2010 | Davis | ............... | G04F 5/14 |
| | | | | 331/3 |
| 2011/0095755 A1 * | 4/2011 | Maki | ............... | G01R 33/032 |
| | | | | 324/244.1 |
| 2011/0297372 A1 * | 12/2011 | Maida, Jr. | ............... | E21B 47/024 |
| | | | | 166/255.2 |
| 2013/0265042 A1 * | 10/2013 | Kawabata | ............... | G01R 33/26 |
| | | | | 324/301 |
| 2014/0184216 A1 * | 7/2014 | Walker | ............... | G01C 19/62 |
| | | | | 324/305 |
| 2014/0306700 A1 * | 10/2014 | Kamada | ............... | G01R 33/26 |
| | | | | 324/244.1 |
| 2015/0330786 A1 * | 11/2015 | Bulatowicz | ............... | G01R 33/26 |
| | | | | 324/301 |
| 2016/0146909 A1 * | 5/2016 | Kawabata | ............... | G01R 33/26 |
| | | | | 324/304 |
| 2016/0313417 A1 * | 10/2016 | Kawabata | ............... | G01R 33/26 |
| 2017/0023654 A1 * | 1/2017 | Kobayashi | ............... | G01R 33/26 |

FOREIGN PATENT DOCUMENTS

| | | |
|---|---|---|
| JP | 2005-072103 A | 3/2005 |
| JP | 2008-153320 A | 7/2008 |
| JP | 2009-128235 | 6/2009 |
| JP | WO 2015015628 A1 * | 2/2015 ............. G01R 33/26 |

* cited by examiner

MAGNETIC FIELD MEASUREMENT DEVICE

TECHNICAL FIELD

The present invention relates to a magnetic field measurement device utilizing the magneto-optical effect due to optical pumping.

BACKGROUND ART

In a magnetic field measurement device utilizing the magneto-optical effect due to optical pumping, a glass cell in which an alkali metal gas (such as potassium, rubidium, or cesium, for example) is enclosed is used as a sensor. A static magnetic field is applied to the glass cell, the energy level of alkali metal in the glass cell is subjected to Zeeman splitting, and interaction between light and magnetism caused by irradiating the glass cell with light obtained by changing the polarization state such as linearly polarized light, circularly polarized light or elliptically polarized light or light obtained by changing the intensity or the phase such as intensity modulated light or phase modulated light is used to detect the magnetism in the glass cell. The light source of pump light with which the glass cell is irradiated needs to be a light source with stabilized frequency to such an extent that is comparable to use in a field of spectroscopic measurement of atoms and molecules.

Various lasers including semiconductor lasers are used for light sources. A laser with frequency stabilization has a mechanism for detecting a frequency deviation from a reference deviation. A signal obtained by detecting a frequency deviation serves as a control signal for frequency stabilization of the laser. Absorption lines of atoms and molecules or an interferometer are used as a target to be the reference frequency.

Japanese Patent Application Laid-Open No. 2005-72103 (PTL 1) discloses a background art relating to frequency stabilization of a laser. PTL 1 discloses a technology for stabilizing a laser frequency utilizing the sub-Doppler spectrum of atoms, and that a simple and appropriate frequency stabilizing laser device as compared to conventional devices is provided.

The light intensities of light sources including semiconductor lasers are typically not always stable. Thus, in an application requiring a stable light intensity, automatic power control (APC) is conducted, in which light generated by a light source is measured by a photodetector, and the light intensity is stabilized by controlling drive current of the light source by the measurement signal.

Japanese Patent Application Laid-Open No. 2008-153320 (PTL 2) discloses a background art using the APC. PTL 2 discloses that a light source system including a light source, a photodetector configured to detect light output from the light source, a light scatterer disposed between optical paths of the light source and the photodetector, and a control/correction' unit configured to control an output of the light source by using a detection result from the photodetector or correct an output variation of the light source is provided.

Japanese Patent Application Laid-Open No. 2002-314187 (PTL 3) also discloses a background art. PTL 3 discloses that a laser diode module is achieved, which includes an optical semiconductor element in which a semiconductor laser and an electro-absorption modulator are integrated, and in which an output of backlight from the semiconductor laser side is input to a photodiode via an optical filter having a wavelength transmission dependency, temperature control is conducted according to an output from the photodiode, and the current of the semiconductor laser is controlled on a basis of an output from the electro-absorption modulator.

CITATION LIST

Patent Literatures

PTL 1: Japanese Patent Application Laid-Open No. 2005-72103
PTL 2: Japanese Patent Application Laid-Open No. 2008-153320
PTL 3: Japanese Patent Application Laid-Open No. 2002-314187

SUMMARY OF INVENTION

Technical Problem

In the laser frequency stabilizing device and the laser frequency stabilizing method disclosed in PTL 1, a gas cell in which gas is encapsulated is used as a target of reference frequency. In a state in which pump light passing through the gas cell is shielded at regular time intervals, probe light is similarly made to enter the gas cell. Frequency stabilization of the laser is conducted by using a first differentiated signal obtained from the difference in intensity of probe light between an ON state and an OFF state of the pump light. During frequency stabilization, control on angle adjustment of optical components such as a diffraction grating or a mirror inside a laser head and control on a current injected to the laser are conducted. Thus, the output light intensity of the laser is not constant and varies continuously.

In the light source system disclosed in PTL 2, light output from the laser is detected by the photodetector via the light scatterer, and the detection signal is used to control the output light intensity of the laser to be stable. Since the current injected to the laser is controlled for stabilization of the output light intensity, the frequency of the laser always varies.

Furthermore, with the laser diode module and the optical transmitter disclosed in PTL 3, an output signal from the photodetector detecting output light from the laser is used to control the temperature of the laser diode and the current injected to the laser diode. Thus, the laser frequency is not always constant like PTL 2 mentioned above.

An object of the present invention is therefore to provide a magnetic field measurement device including a light source capable of both laser frequency stabilization and output light intensity stabilization.

A magnetic field measurement device according to an exemplary embodiment of the present invention is an optically pumped magnetic sensor utilizing magneto-optical characteristics of spin-polarized alkali metal, and a glass cell enclosed with alkali metal is used as a sensor unit. The optically pumped magnetic sensor includes a light source unit for emitting pump light to the sensor unit, a coil unit for applying a static magnetic field and a RF magnetic field to the sensor unit, and a signal control processor, wherein the sensor unit and the coil unit are within a magnetic shield. For the light source of pump light, a laser having a mechanism for adjusting a laser cavity length at high speed and with high accuracy is used; typically, an external cavity diode laser is used. The light source unit includes, in addition to a frequency stabilization unit configured to feed back a frequency stabilization control signal based on a phase detection signal of an output light from the laser to a cavity length adjustment mechanism of the laser and a supply source of current injected to the laser, an intensity stabilization unit configured to control an optical modulator that receives the output light from the laser so that an output light intensity of the optical modulator becomes a predetermined value, and emits pump light with stable intensity and stable frequency to the sensor unit via a polarization maintaining optical fiber. As a result of using a light source unit having an intensity stabilization unit configured to control an optical modulator that receives output light from a laser so that the intensity of light having passed through the optical modulator becomes a predetermined value independently of a frequency stabilization unit configured to control the cavity length of the laser as described above, pump light with both stabilized frequency and stabilized output light intensity is achieved, and the measurement sensitivity and the measurement accuracy of a magnetic measurement device are achieved. Typically, the optical modulator of the intensity stabilization unit is provided before a beam splitter that inputs a light beam resulting from dividing laser output light to a reference glass cell for detecting the phase of the output light. Thus, the intensity stabilization unit of the light source unit is provided in a control loop formed by the frequency stabilization unit.

In another embodiment, the optical modulator of the intensity stabilization unit is provided subsequent to a beam splitter that inputs a light beam resulting from dividing laser output light to a reference glass cell for detecting the phase of the output light. Thus, the intensity stabilization unit is present outside of a control loop formed by the frequency stabilization unit, and pumping light is adjusted in the order of frequency stabilization and intensity stabilization.

Advantageous Effects of Invention

The present invention provides lower noise and stable operation of an optically pumped magnetic sensor with a device configuration capable of achieving both of intensity stabilization of a light source and frequency stabilization thereof.

DESCRIPTION OF EMBODIMENTS

Embodiment 1

Figure 1:
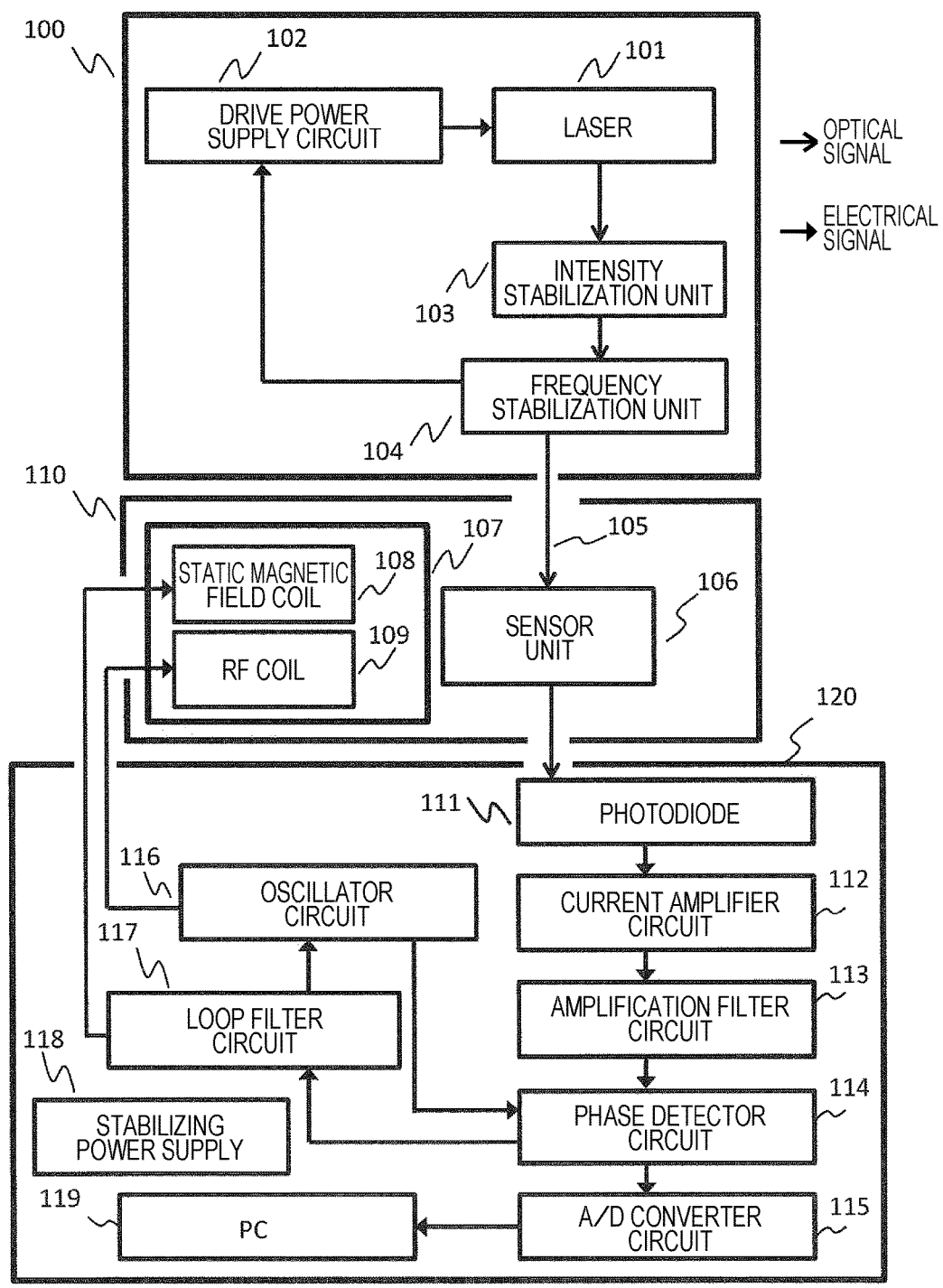
FIG. 1 is a block diagram illustrating an overall configuration of a magnetic field measurement device including an optically pumped magnetic sensor that is a first embodiment of the present invention.

FIG. 1 illustrates an overall configuration of a magnetic field measurement device of an embodiment (Embodiment 1) of the present invention. The magnetic field measurement device includes a light source unit 100, a coil unit 107, a sensor unit 106, a magnetic shield unit 110, and a signal control processor 120. The light source unit 100 includes a laser 101, a drive power supply circuit 102, an intensity stabilization unit 103, and a frequency stabilization unit 104, and generates sensor pump light 105 to be introduced to a sensor glass cell in which alkali metal gas is encapsulated in the sensor unit 106. The light source is preferably a laser rather than a lamp in view of stability and performance. A laser is thus used for the light source in the present embodiment.

In the operation of the optically pumped magnetic sensor, the laser needs to oscillate in a single mode with an oscillation frequency including absorption lines ($D_1$ line, $D_2$ line) of alkali metals and a spectral line width equal to or smaller than absorption line widths of alkali metals. Thus, in view of practicality (low cost, small size) in addition to required laser operating conditions, the laser used herein is a semiconductor laser. Among diode lasers, an external cavity diode laser including optical components such as a diffraction grating outside of a laser element, or a distributed-feedback laser (DFB laser) or a distributed Bragg reflector laser (DBR laser) including a cavity length adjusting structure inside a laser element is preferably used.

The laser 101 is driven by the drive power supply circuit 102 to oscillate. A Peltier element is used for thermostatic control at a preset temperature so that the laser element oscillates at a desired oscillation frequency. When an external cavity diode laser is used, a current value injected to the laser element is set and the cavity length of an external resonator including optical components such as a diffraction grating is adjusted in addition to temperature control of the laser element, so that mode-hopping that is great deviation of the oscillation frequency of the laser from absorption lines of alkali metals will not occur. Similarly, when a DFB laser or a DBR laser is used, a current value injected to the laser element is set in addition to temperature control of the laser element so that mode hopping is prevented.

Figure 2:
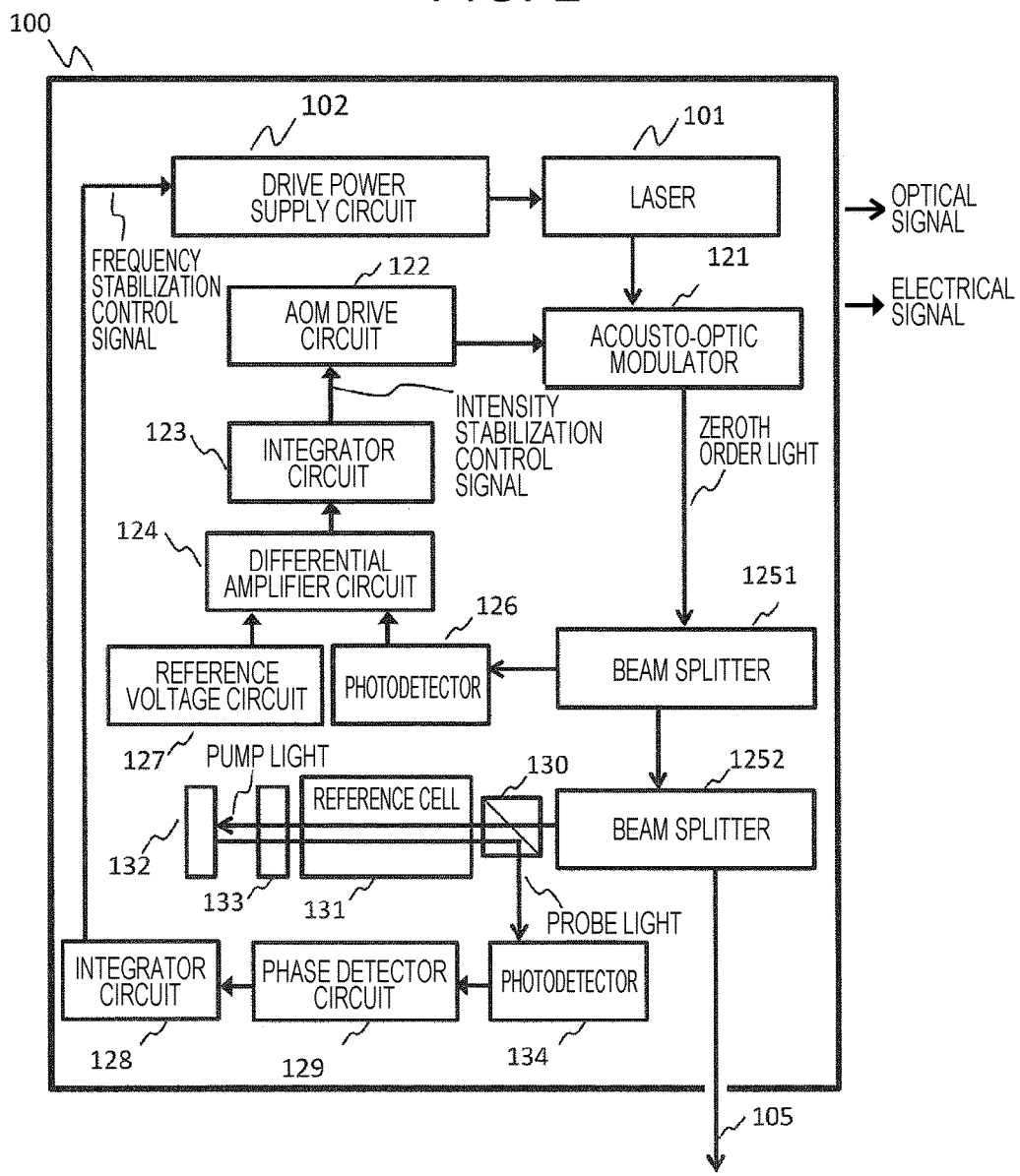
FIG. 2 is a block diagram illustrating a light source unit including intensity stabilization and frequency stabilization mechanisms for the magnetic field measurement device.

FIG. 2 illustrates a detailed configuration of the light source unit 100 of the magnetic field measurement device in Embodiment 1. Laser light output from the laser 101 enters an acousto-optic modulator (AOM) 121. The laser light is divided into zeroth order light, first order light, ..., and N-th order light (N is an integer) by Bragg diffraction and emitted from the AOM. At this point, the angle of the laser light entering the AOM 121 is adjusted so that the first order light will be maximum. For the adjustment of the incident laser light, a position adjustment mechanism in three axes (X axis, Y axis, and Z axis) and an angle (θaxis), for example, provided in the AOM 121 allows the adjustment to be easier. The zeroth order light is used for the laser light emitted from the AOM 121; and the zeroth order light is divided into two beams by a beam splitter 1251.

One of the zeroth order light beams resulting from the division is detected by a photodetector 126 to be used for intensity stabilization of the laser light. An output voltage of the photodetector 126 and an output voltage Of a reference voltage circuit 127 provided external thereto are input to a differential amplifier circuit 124. In this configuration, the output voltage of the differential amplifier circuit 124 is input to an AOM drive circuit 122 via an integrator circuit 123. With this configuration, control for intensity stabilization of the laser light is performed. Note that the AOM can also function as laser light intensity adjustment, and adjusts the output voltage of the reference voltage circuit 127 for adjusting the intensity.

The other of the zeroth order light beams resulting from the division is further divided into two laser light beams by a beam splitter 1252. The laser light beams resulting from the division are used for frequency stabilization of the laser light and for sensor pump light. For frequency stabilization of the laser light, the absorption lines of alkali metals or an interferometer described above in the background art can be used as a basis for frequency stabilization. With use of an interferometer, best frequency stability can be obtained. In terms of convenience and cost, however, frequency stabilization using the absorption lines of alkali metals is preferable. Furthermore, since the absorption lines of alkali metal atoms has a range of several hundred MHz even at room temperature (24° C., for example) owing to thermal motion. Frequency stabilization is sufficient performance if its stabilization is keeping within the range of the natural width of alkali metal metals (about 5 MHz for cesium atom, for example). Thus, for frequency stabilization in the present embodiment, frequency stabilization using practical absorption lines of alkali metal atoms is employed, and among such frequency stabilization, the saturated absorption spectroscopy that is deemed typical is used.

Specifically, the laser light beam for frequency stabilization resulting from the division by the beam splitter 1252 enters a reference glass cell 131 in which only alkali metal is contained so that the absorption line of the alkali metal is obtained. On a side opposite to the side on which the laser light is incident, an ND filter 133 and a mirror 132 are provided in layers. This structure allows laser light that has passed through the reference glass cell 131 to be reflected by the mirror, returned with decreased intensity to the reference glass cell 131, and travels through a path along the path of the incident laser light in opposite direction. Thus, the incident laser light (pump light) has a high light intensity, the reflected laser light (probe light) has an intensity sufficiently lower than that of the pump light, and the paths of the pump light and the probe light overlap with each other. Pumping of alkali metal atoms is saturated by the pump light with a high laser light intensity and the frequency of the probe light is swept, so that absorption of probe light is decreased with the resonant frequency of the alkali metal atoms under saturation. As a result, a sharp valley is caused in the light absorption frequency characteristic at the reference glass cell. The line width of the valley is the natural width of the alkali metal atoms, and the frequency is stabilized by locking the laser frequency to the bottom of the valley or the slope. Details of a control loop for the frequency stabilization in a chase where an external resonator semiconductor laser is used for the laser 101 will be described. The external resonator semiconductor laser includes a piezoelectric element positioned to face the laser element and configured to minutely change the angle of the diffraction grating forming a resonator, or a piezoelectric element configured to minutely change the angle of a mirror provided on an optical path of diffracted light from the diffraction grating. A laser having the former structure is called a Littrow laser and a laser having the latter structure is called a Littman laser. In either case, the frequency of the laser can be adjusted by adjusting the cavity length with the voltage applied to the piezoelectric element. For stabilizing the frequency to the bottom of the valley of the light absorption frequency characteristic of the reference cell, that is, to the peak of the frequency characteristic of light having passed through the reference glass cell 131, a voltage signal of the piezoelectric element for adjusting the above-described cavity length is modulated when the laser frequency is swept, and a distributed error signal obtained by detecting a modulated component by a phase detector circuit 129 is made to pass through an integrator circuit 128 and fed back to the current injected to the piezoelectric element and the laser element. For stabilizing the frequency to the slope, the tilt of the slope within a range in which the slope is linear is made to pass through the integrator circuit as an error signal, and fed back to the current injected to the piezoelectric element and the laser element.

The other laser light beam resulting from division of the zeroth order light is laser light whose frequency and intensity are stabilized as a result of the intensity stabilization and the frequency stabilization, is introduced into a magnetic shield 110 and becomes pump light for the sensor unit 106.

The sensor unit 106 is installed inside the magnetic shield 110 together with a source of the magnetic field to be measured. Inside the magnetic shield 110, a static magnetic field coil 108 that applies a static magnetic field in a direction at an angle of 45 degrees with respect to the optical axis of the pump light to the glass cell of the sensor unit 106 and an RF coil 109 that generates an oscillating magnetic field in a direction perpendicular to the static magnetic field are further included.

Figure 3:
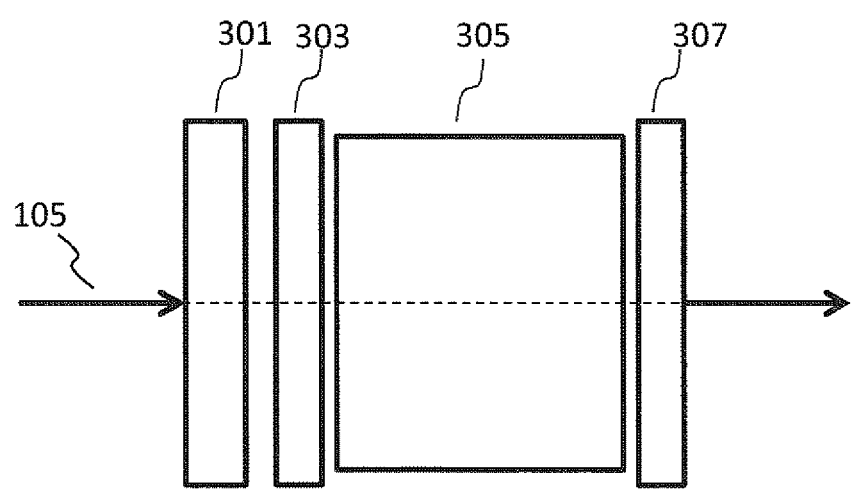
FIG. 3 is a side view illustrating a structure of a magnetic sensor of the magnetic field measurement device.

FIG. 3 illustrates a main structure of the sensor unit 106. In the sensor unit 106, components in FIG. 3 are arranged as illustrated inside a non-magnetic mold, which is not illustrated. The sensor pump light guided from the light source unit by an optical fiber is introduced into the sensor glass cell 305 via a collimating lens 301 and a $\lambda/4$ wavelength plate 303. The pump light is converted into parallel light by the collimating lens 301, and converted into circularly polarized light by the $\lambda/4$ wavelength plate 303, and enters the sensor glass cell 305. The laser light having passed through the sensor glass cell 305 is collected by a condenser lens 307, guided to a photodiode 111 provided in the signal processor 120 of FIG. 1 and detected. The sensor pump light may enter the sensor glass cell as space propagating light, but is preferably guided to the sensor glass by a polarization maintaining optical fiber in view of practicality. In addition, a polarizer or a $\lambda/2$ wavelength plate may be placed between the collimating lens 301 and the $\lambda/4$ wavelength plate 303 in order to adjust linearly polarized light. The laser light having passed through the sensor glass cell 305 may not only be detected directly by the photodetector but also be guided to the photodiode 111 via an optical fiber. In order to achieve high coupling efficiency, a multimode optical fiber having a large core diameter is preferably used. The multimode optical fiber typically has no polarization plane maintaining function. Since, however, reduction in polarization, which is a problem for the light entering the glass cell of the sensor unit, is not a problem in light quantity detection of detected light, use of the multimode optical fiber does not cause any problem. The signal processor 120 further includes a current amplifier circuit 112, an amplification filter circuit 113, a phase detector circuit 114, an A/D converter circuit 115, an oscillator circuit 116, a loop filter circuit 117, a stabilizing power supply 118, and a PC 119. A current signal output from the photodiode 111 is converted to a voltage signal by the current amplifier circuit 112, and adjusted to have a gain and a band required for measurement at the amplification filter circuit 113. The phase detector circuit 114 detects an output of the amplification filter circuit 113 with use of a signal from the oscillator circuit 116 as a reference signal. The detected phase signal is controlled by the loop filter circuit 117 so as not to oscillate, and an output of the loop filter circuit 117 is input to the oscillator circuit 116 to control the oscillation frequency with the voltage, so that the frequency of a RF magnetic field to be applied to the sensor unit 106 is feedback controlled. The variation of the output of the phase detector circuit 114 in feedback control allows a weak magnetic field generated at an object to be measured near the sensor glass cell 305 to be measured. While the photodiode 111 and the current amplifier circuit 112 are typically connected to each other by a shielded cable, the photodiode 111 and the current amplifier circuit 112 are more preferably integrated to be a structure resistant to electromagnetic noise.

With the configuration described above, a magnetic measurement device capable of eliminating both light intensity variation and frequency variation of laser light for pumping introduced into a magnetic sensor unit, and capable of optical pumping magnetic measurement with high accuracy with use of a stable pump light source can be achieved.

Embodiment 2

Figure 4:
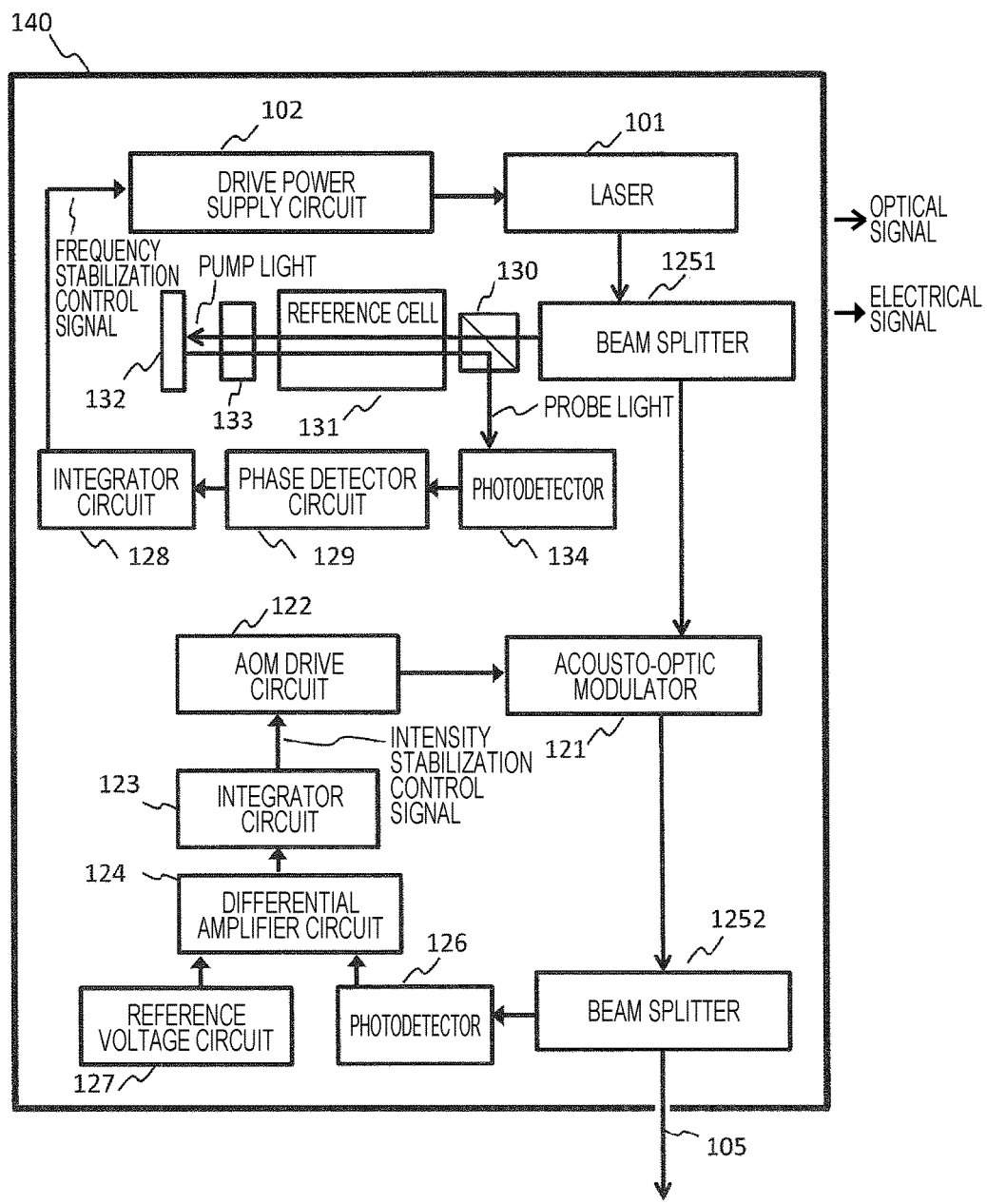
FIG. 4 is a block diagram illustrating a configuration of a light source unit of a magnetic field measurement device including an optically pumped magnetic sensor that is a second embodiment of the present invention.

A magnetic measurement device of the second embodiment (Embodiment 2) of the present invention is different from that of Embodiment 1 in the configuration of the light source unit. The magnetic measurement device has the same configuration as that of the magnetic measurement device of Embodiment 1 illustrated in FIG. 1 except for the light source unit. Hereinafter, the configuration of a light source unit 140 of the magnetic measurement device of Embodiment 2 will be described with reference to FIG. 4. Components that are the same as those of the light source unit of Embodiment 1 illustrated in FIG. 2 will be designated by the same reference numerals. As compared to the light source unit of Embodiment 1, the difference lies in that the intensity stabilization unit constituted by the photodetector 126, the reference voltage circuit 127, the differential amplifier 124, the integrator circuit 123, the AOM drive circuit 122, and the acousto-optic modulator 121 is not inside of the control loop for frequency stabilization from the frequency stabilization unit, through the drive power supply circuit 102, and back to the laser 101 but subsequent to the control loop. Specifically, one of light beams obtained by dividing laser light, which has been output by the laser 101 that is a light source, by the first beam splitter 1251 is introduced to a layered structure of a half mirror 130, the reference cell 131, the ND filter 133, and the mirror 132. An extraction signal of a modulated component of the cavity length of the laser obtained by detecting an output of the photodetector 134 by the phase detector circuit 129 is integrated by the integrator circuit 128, fed back to the drive power supply circuit 102 of the laser, and functions as a frequency stabilization control signal for the laser 101. The other light beam obtained by dividing the laser light subjected to frequency stabilization by the control loop is guided from the beam splitter 1251 to the acousto-optic modulator 121. The acousto-optic modulator 121 is controlled by an intensity stabilization control signal obtained by a control circuit constituted by the photodetector 126 configured to detect light beams from the second beam splitter 1252, the reference voltage circuit 127, the differential amplifier 124, the integrator circuit 123, the AOM drive circuit 122, and output light from the acousto-optic modulator 121 is thus controlled constant. As described above, control loops are formed in the order of the frequency stabilization unit and the intensity stabilization unit, and the sensor pump light 105 is obtained through the control loops.

The configuration subsequent to the sensor glass cell to which the pump light 105 is introduced is the same as that of Embodiment 1, and it is also possible according to the present embodiment to eliminate both light intensity variation and frequency variation of laser light for pumping and to perform optical pumping magnetic measurement with high accuracy with use of a stable pump light source.

Embodiment 3

In the third embodiment (Embodiment 3) of the present invention, pump light introduced into the sensor glass cell is not single wavelength laser light as in Embodiment 1, but mixed light of laser light beams with a $D_1$ line and a $D_2$ line that are absorption lines of alkali metal used in the sensor glass cell is used as pump light.

Figure 5:
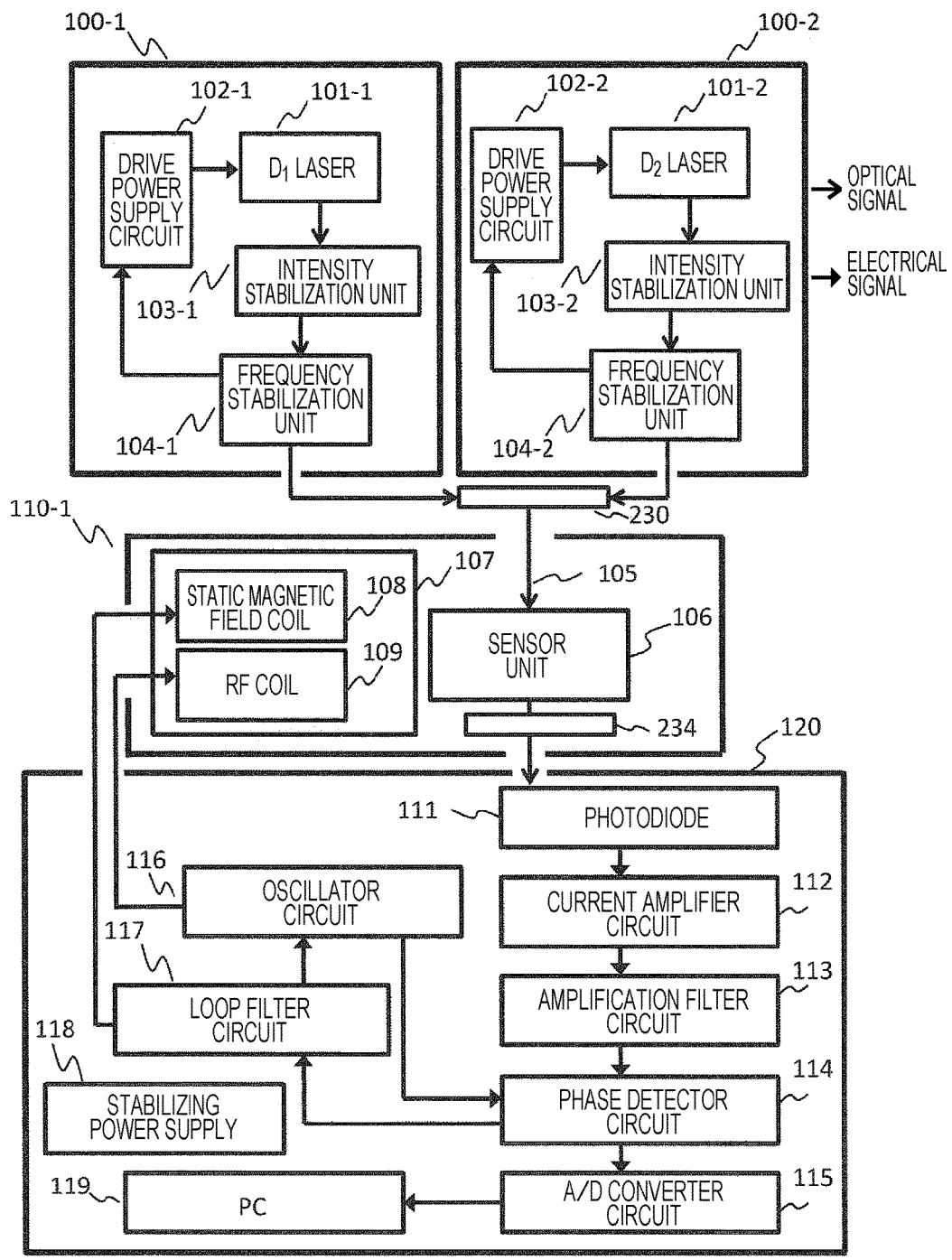
FIG. 5 is a block diagram illustrating an overall configuration of a magnetic field measurement device including an optically pumped magnetic sensor that is a third embodiment of the present invention.

FIG. 5 illustrates an overall configuration of a magnetic measurement device of Embodiment 3. Light source units 100-1 and 100-2 independent of each other are provided. The light source unit 100-1 includes a $D_1$ line laser 101-1, an intensity stabilization unit 103-1, a frequency stabilization unit 104-1, and a drive power supply circuit 102-1, and the detailed configuration thereof is the same as that of the light source unit 100 of Embodiment 1 illustrated in FIG. 2. Similarly, the light source unit 100-2 also includes a $D_2$ line laser 101-2, an intensity stabilization unit 103-2, a frequency stabilization unit 104-2, and a drive power supply circuit 102-2, and the detailed configuration thereof is also the same as that of the light source unit 100 of Embodiment 1 illustrated in FIG. 2. Thus, in each of the light source units, the structure up to intensity stabilization and frequency stabilization of laser light is the same as that of Embodiment 1 in FIG. 1.

The laser light beams that have undergone intensity stabilization and frequency stabilization are converted into parallel light beams by the collimating lens, and then converted into circularly polarized light beams through the λ/4 wavelength plate. The laser light beams converted into the circularly polarized light beams are coaxially combined with use of a half mirror 230 to obtain the mixed light. The mixed light enters a sensor cell provided in a magnetic shield 110-1. The configuration inside the magnetic shield 110-1 is different from that of the magnetic shield of Embodiment 1 in that a diffraction grating 234 which laser light having passed through the sensor glass cell enters is provided. The diffraction grating 234 is used to divide the laser light having passed through the glass cell into a $D_1$ laser light beam and a $D_2$ laser light beam, extract only one of the laser light beams and detect the laser light beam as a signal for magnetic measurement. The configuration and the operation of the signal processor 120 Subsequent to the photodiode 111 that detects the extracted laser light are the same as that of Embodiment 1.

Thus, in the present embodiment, the combined $D_1$ laser light beam and $D_2$ laser light beam are used as pump light, one of the laser light beams is pump-probe light for magnetic measurement, and the other of the laser light beams functions as repump light for improving the signal-to-noise ratio of a magnetic measurement signal. With the magnetic measurement device of Embodiment 3, atoms in a ground state level F4 and atoms in a ground state level F3 can be pumped among the alkali metal atoms (cesium atoms, for example) in the sensor glass cell. The magnetic measurement device of Embodiment 3 thus has an advantageous effect of further improving the magnetic detection sensitivity of an optically pumped magnetometer as compared to the devices of Embodiments 1 and 2.

Either of the $D_1$ laser light beam and the $D_2$ laser light beam can be used for the pump-probe light. That is, the same applies to the repump light. It is, however, more effective to use the $D_1$ laser light beam for the pump-probe light and the $D_2$ laser light beam for the repump light. This is because the $D_1$ line has a wider energy transfer interval of alkali metal atoms than the $D_2$, line and the influence of another energy transfer close to the energy transfer being used can thus be reduced.

Embodiment 4

Figure 6:
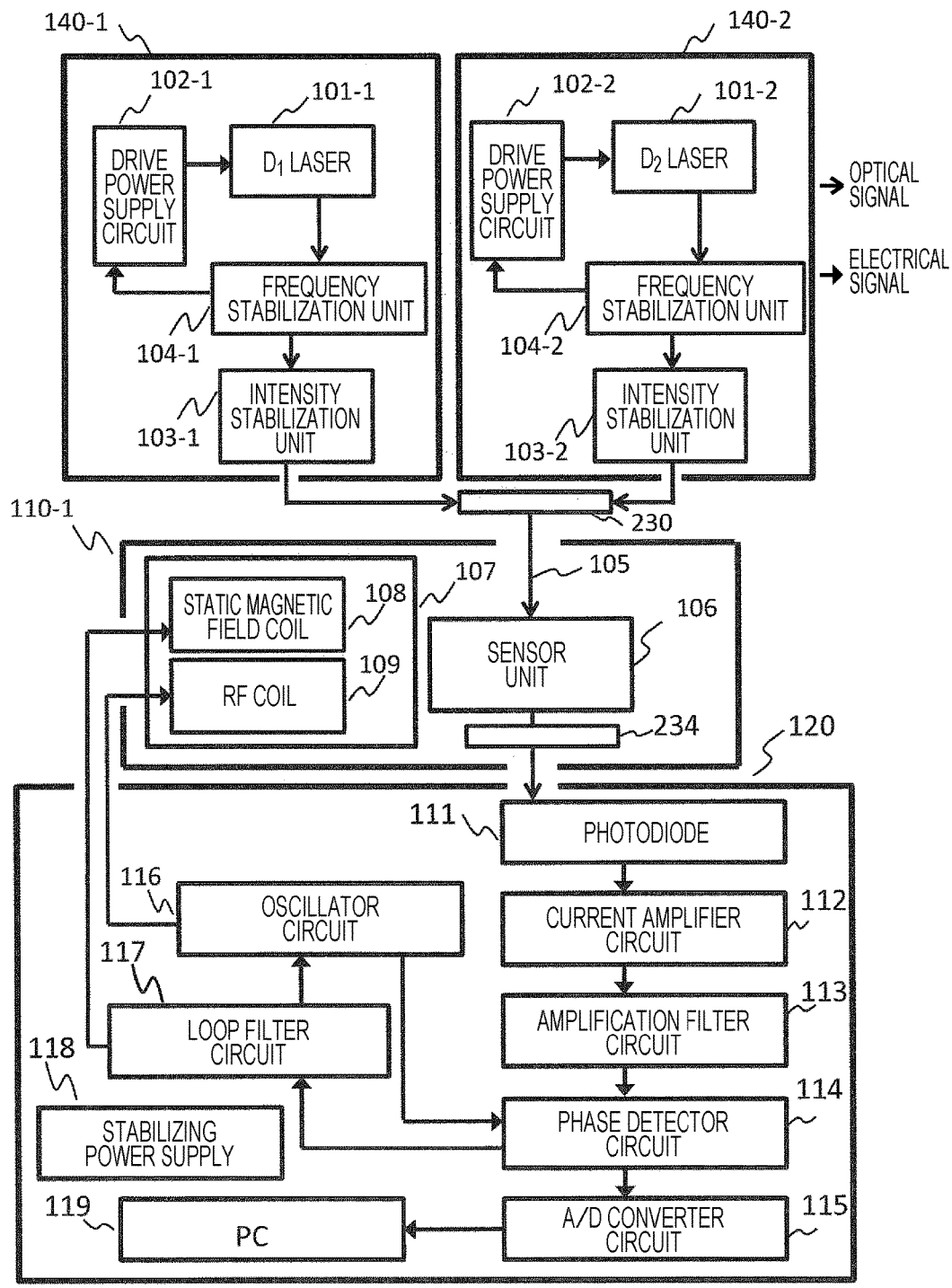
FIG. 6 is a block diagram illustrating an overall configuration of a magnetic field measurement device including an optically pumped magnetic sensor that is a fourth embodiment of the present invention.

FIG. 6 illustrates an overall configuration of a magnetic measurement device of a fourth embodiment (Embodiment 4) of the present invention. In the magnetic measurement device of the present embodiment, mixed light of laser light beams with a $D_1$ line and a $D_2$ line that are absorption lines of alkali metal used in the sensor glass cell is used as pump light, similarly to Embodiment 3. Light source units 140-1 and 140-2 that generate $D_1$ laser light and $D_2$ laser light are thus provided. These light source units do not include intensity stabilization units inside of the control loops for frequency stabilization like the light source unit of Embodiment 1. The intensity stabilization units 103-1 and 103-2 are provided subsequent to a control loop formed by the frequency stabilization unit 104-1 and the control loop formed by the frequency stabilization unit 104-2, respectively. Detailed configurations of the light source units 140-1 and 140-2 are the same as that illustrated in FIG. 4. Note that FIG. 6 illustrates the inside of the light source units 140-1 and 140-2 in an outline block configuration. The $D_1$ laser light beam from the light source unit 140-1 and the $D_2$ laser light beam from the light source unit 140-2 are converted into circularly polarized light beams parallel to each other by the collimating lens and the λ/4 wavelength plate, and coaxially combined by the half mirror 140 to be mixed light, similarly to Embodiment 3. Furthermore, the configuration in which laser light having passed through the sensor glass cell of the sensor unit 106 is made to pass through the diffraction grating 234 so that either one of the $D_1$ laser light beam and the $D_2$ laser light beam is extracted and detected is also the same as that of the magnetic measurement device of Embodiment 3.

Embodiment 5

Figure 7:
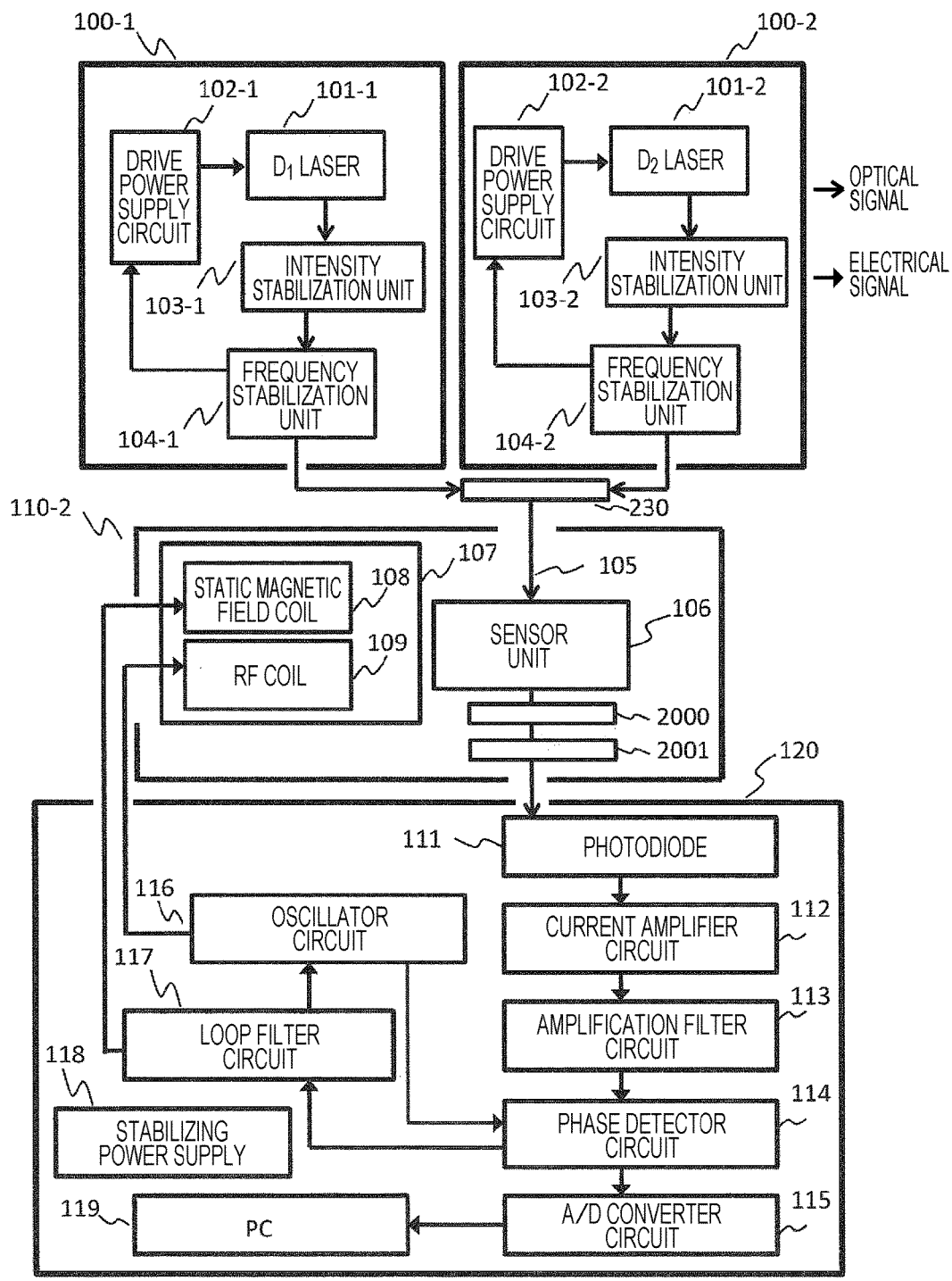
FIG. 7 is a block diagram illustrating an overall configuration of a magnetic field measurement device including an optically pumped magnetic sensor that is a fifth embodiment of the present invention.

FIG. 7 illustrates an overall configuration of a magnetic measurement device of a fifth embodiment (Embodiment 5) of the present invention. In the magnetic measurement device of the present embodiment, mixed light of laser light beams with a $D_1$ line and a $D_2$ line that are absorption lines of alkali metal used in the sensor glass cell is used as pump light, similarly to Embodiment 3. Light source units 140-1 and 140-2 that generate $D_1$ laser light and $D_2$ laser light are thus provided. The structure up to intensity stabilization and frequency stabilization of laser light and the device configuration for guiding pump light to the sensor unit are the same as those of Embodiment 3 illustrated in FIG. 5.

The laser light beams that have undergone intensity stabilization and frequency stabilization are converted into parallel light beams by the collimating lens, and then converted into circularly polarized light beams through the λ/4 wavelength plate. The laser light beams converted into the circularly polarized light beams are coaxially combined with use of a half mirror 230 to obtain the mixed light. The mixed light enters a sensor cell provided in a magnetic shield 110-2. The configuration inside the magnetic shield 110-2 is different from that of the magnetic shield of Embodiment 3 in that a λ/4 wavelength plate 2000 and a polarization beam splitter 2001 are provided instead of the diffraction grating 234 which laser light having passed through the sensor glass cell enters. The $D_1$ laser light beam and the $D_2$ laser light beam having passed through the glass cell are converted from the circularly polarized light beams to linearly polarized light beams by the λ/4 wavelength plate 2000. The $D_1$ laser light beam and the $D_2$ laser light beam that are linearly polarized light beams resulting from the conversion are divided into the $D_1$ laser light beam and the $D_2$ laser light beam by the polarization beam splitter 2001, and only one of the laser light beam is extracted and detected as a signal for magnetic measurement. The configuration and the operation of the signal processor 120 subsequent to the photodiode 111 that detects the extracted laser light are the same as that of Embodiment 3.

Embodiment 6

Figure 8:
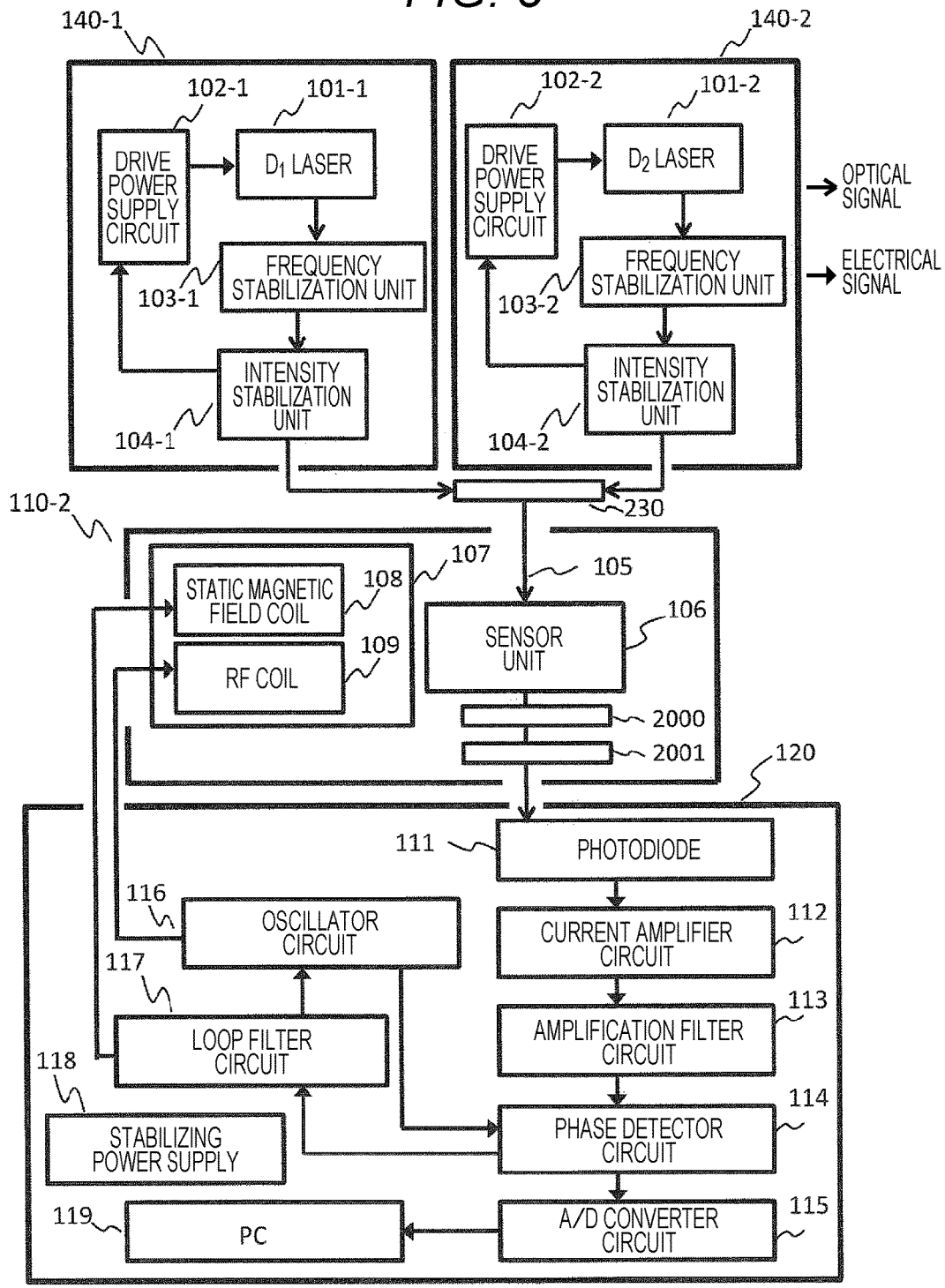
FIG. 8 is a block diagram illustrating an overall configuration of a magnetic field measurement device including an optically pumped magnetic sensor that is a sixth embodiment of the present invention.

FIG. 8 illustrates an overall configuration of a magnetic measurement device of a sixth embodiment (Embodiment 6) of the present invention. In the magnetic measurement device of the present embodiment, mixed light of laser light beams with a $D_1$ line and a $D_2$ line that are absorption lines of alkali metal used in the sensor glass cell is used as pump light, similarly to Embodiment 3. Light source units 140-1 and 140-2 that generate $D_1$ laser light and $D_2$ laser light are thus provided. The structure up to intensity stabilization and frequency stabilization of laser light and the device configuration for guiding pump light to the sensor unit are the same as those of Embodiment 3 illustrated in FIG. 5.

These light source units do not include intensity stabilization units inside of the control loops for frequency stabilization like the light source unit of Embodiment 5. The intensity stabilization units 103-1 and 103-2 are provided subsequent to a control loop formed by the frequency stabilization unit 104-1 and the control loop formed by the frequency stabilization unit 104-2, respectively. Detailed configurations of the light source units 140-1 and 140-2 are similar to those illustrated in FIG. 6. Furthermore, the configuration inside the magnetic shield 110-2 is the same as that of Embodiment 5. The $D_1$ laser light beam from the light source unit 140-1 and the $D_2$ laser light beam from the light source unit 140-2 are converted into circularly polarized light beams parallel to each other by the collimating lens and the λ/4 wavelength plate, and coaxially combined by the half mirror 140 to be mixed light, similarly to Embodiment 5. Furthermore, the configuration in which laser light having passed through the sensor glass cell of the sensor unit 106 is made to pass through λ/4 wavelength plate 2000 and the polarization beam splitter 2001 so that either one of the $D_1$ laser light beam and the $D_2$ laser light beam is extracted and detected is also the same as that of the magnetic measurement device of Embodiment 5.

REFERENCE SIGNS LIST

100, 140, 100-1, 100-2, 140-1, 140-2 light source unit
101 laser
101-1 $D_1$ laser
101-2 $D_2$ laser
102, 102-1, 102-2 drive power supply circuit
103, 103-1, 103-2 intensity stabilization unit
104, 104-1, 104-2 frequency stabilization unit
105 sensor pump light
106 sensor unit
107 coil unit
108 static magnetic field coil
109 RF coil 110, 110-1, 110-2 magnetic shield
111 photodiode
112 current amplifier circuit
113 amplification filter circuit
114 phase detector circuit
115 A/D converter circuit
116 oscillator circuit
117 loop filter circuit
118 stabilizing power supply
119 PC
120 signal control processor
121 acousto-optic modulator (AOM)
122 AOM drive circuit
123, 128 integrator circuit
124 differential amplifier circuit
126, 134 photodetector
127 reference voltage circuit
129 phase detector circuit
130 half mirror
131 reference cell
132 mirror
133 ND filter
230 half mirror
234 diffraction grating
301 collimating lens
303, 2000 λ/4 wavelength plate
305 sensor glass cell
307 condenser lens
1251, 1252 beam splitter
2001 polarization beam splitter

The invention claimed is:

1. A magnetic field measurement device comprising:
a magnetic sensor unit disposed in a magnetically shielded space, including a glass cell having alkali metal gas encapsulated therein, and configured to detect a magnetic field with use of a magneto-optical characteristic of spin-polarized alkali metal;
a light source unit configured to generate pump light and introduce the pump light into the glass cell;
a coil unit provided in the magnetically shielded space, and including a plurality of coils configured to apply a static magnetic field and a RF magnetic field to the magnetic sensor unit; and
a signal processor configured to perform lock-in detection of a light detection signal of light transmitted through the glass cell, control an intensity of the static magnetic field and a frequency of the RF magnetic field generated by the coil unit according to a lock-in detection output, and obtain a measurement signal reflecting a magnetic field intensity of an object to be measured installed in the magnetically shielded space,
wherein the light source unit includes:
a laser configured to output light;
an optical modulator configured to modulate the output light from the laser;
a first beam splitter disposed to split modulated light output from the optical modulator into a first light beam and a second light beam;
an intensity stabilization unit configured to control an output light intensity of the optical modulator to become a predetermined value based on the first light beam;
a second beam splitter disposed to split the second light beam into a third light beam and a fourth light beam; and
a frequency stabilization unit configured to generate a frequency stabilization control signal which controls a cavity length of the laser corresponding to an output frequency of the laser based on a phase of light obtained from a reference glass cell that receives the third light beam, and
wherein the pump light is the fourth light beam.

2. A magnetic field measurement device comprising:
a magnetic sensor unit disposed in a magnetically shielded space, including a glass cell having alkali metal gas encapsulated therein, and configured to detect a magnetic field with use of a magneto-optical characteristic of spin-polarized alkali metal;
a light source unit configured to generate pump light and introduce the pump light into the glass cell;
a coil unit provided in the magnetically shielded space, and configured to apply a static magnetic field and a RF magnetic field to the magnetic sensor unit; and
a signal processor configured to perform lock-in detection of a light detection signal of light transmitted through the glass cell, control an intensity of the static magnetic field and a frequency of the RF magnetic field generated by the coil unit according to a lock-in detection output, and obtain a measurement signal reflecting a magnetic field intensity of an object to be measured installed in the magnetically shielded space,
wherein the light source unit includes:
a laser configured to output light;
a first beam splitter disposed to split the output light from the laser into a first light beam and a second light beam;
a frequency stabilization unit configured to generate a frequency stabilization control signal which controls a cavity length of the laser corresponding to an output frequency of the laser based on a phase of light obtained from a reference glass cell that receives the first light beam;
an optical modulator configured to modulate the second light beam;
a second beam splitter disposed to split modulated light from the optical modulator into a third light beam and a fourth light beam;
an intensity stabilization unit configured to control an output light intensity of the optical modulator to become a predetermined value based on the third light beam, and
wherein the pump light is the fourth light beam.

3. A magnetic field measurement device comprising:
a magnetic sensor unit disposed in a magnetically shielded space, including a glass cell having alkali metal gas encapsulated therein, and configured to detect a magnetic field with use of a magneto-optical characteristic of spin-polarized alkali metal;
a first light source unit configured to generate laser light of a D1 line that is an absorption line of the alkali metal;
a second light source unit configured to generate laser light of a D2 line that is an absorption line of the alkali metal;
a half mirror disposed to introduce pump light obtained by coaxially combining the laser light of the D1 line from the first light source unit and the laser light of the D2 line from the second light source unit into the glass cell of the magnetic sensor unit;
a coil unit disposed in the magnetically shielded space and including a plurality of coils configured to apply a static magnetic field and an RF magnetic field to the magnetic sensor unit;
a diffraction grating disposed to extract either one of the D1 line and the D2 line of light beams transmitted through the glass cell of the magnetic sensor unit; and a signal processor configured to perform lock-in detection of a detection signal of light extracted by the diffraction grating, control an intensity of the static magnetic field and a frequency of the RF magnetic field generated by the coil unit according to a lock-in detection output, and obtain a measurement signal reflecting a magnetic field intensity of an object to be measured installed in the magnetically shielded space, wherein each of the first and second light source units includes:

a laser configured to output light;

an optical modulator configured to modulate the output light from the laser;

a first beam splitter disposed to split modulated light output from the optical modulator into a first light beam and a second light beam;

an intensity stabilization unit configured to control an output light intensity of the optical modulator to become a predetermined value based on the first beam of light;

a second beam splitter disposed to split the second light beam into a third light beam and a fourth light beam; and a frequency stabilization unit configured to generate a frequency stabilization control signal which controls a cavity length of the laser corresponding to an output frequency of the laser based on a phase of light obtained from a reference glass cell that receives the third light beam, and wherein the first light source unit outputs the fourth light beam as the laser light of the D1 line subjected to intensity stabilization and frequency stabilization and the second light source unit outputs the fourth light beam as the laser light of the D2 line subjected to intensity stabilization and frequency stabilization.

4. A magnetic field measurement device comprising:

a magnetic sensor unit disposed in a magnetically shielded space, including a glass cell having alkali metal gas encapsulated therein, and configured to detect a magnetic field with use of a magneto-optical characteristic of spin-polarized alkali metal;

a first light source unit configured to generate laser light of a D1 line that is an absorption line of the alkali metal;

a second light source unit configured to generate laser light of a D2 line that is an absorption line of the alkali metal;

a half mirror disposed to introduce pump light obtained by coaxially combining the laser light of the D1 line from the first light source unit and the laser light of the D1 line from the second light source into the glass cell of the magnetic sensor unit;

a coil unit disposed in the magnetically shielded space and including a plurality of coils configured to apply a static magnetic field and an RF magnetic field to the magnetic sensor unit;

a diffraction grating disposed to extract either one of the D1 line and the D2 line of light beams transmitted through the glass cell of the glass cell of the magnetic sensor unit; and a signal processor configured to perform lock-in detection of a detection signal of light extracted by the diffraction grating, control an intensity of the static magnetic field and a frequency of the RF magnetic field generated by the coil unit according to a lock-in detection output, and obtain a measurement signal reflecting a magnetic field intensity of an object to be measured installed in the magnetically shielded space, wherein each of the first and second light source units includes:

a laser configured to output light;

a first beam splitter disposed to split the output light from the laser into a first light beam and a second light beam;

a frequency stabilization unit configured to generate a frequency stabilization control signal which controls a cavity length of the laser corresponding to an output frequency of the laser based on a phase of light obtained from a reference glass cell that receives the first light beam;

an optical modulator configured to modulate the second light beam;

a second beam splitter disposed to split modulated light from the optical modulator into a third light beam and a fourth light beam; and an intensity stabilization unit configured to control an output light intensity of the optical modulator to become a predetermined value based on the third light beam, and wherein the first light source unit outputs the fourth light beam as the laser light of the D1 line subjected to intensity stabilization and frequency stabilization and the second light source unit outputs the fourth light beam as the laser light of the D2 line subjected to intensity stabilization and frequency stabilization.

5. A magnetic field measurement device comprising:

a magnetic sensor unit disposed in a magnetically shielded space, including a glass cell having alkali metal gas encapsulated therein, and configured to detect a magnetic field with use of a magneto-optical characteristic of spin-polarized alkali metal;

a first light source unit configured to generate laser light of a D1 line that is an absorption line of the alkali metal;

a second light source unit configured to generate laser light of a D2 line that is an absorption line of the alkali metal;

a half mirror disposed to introduce pump light obtained by coaxially combining the laser light of the D1 line from the first light source unit and the laser light of the D1 line from the second light source into the glass cell of the magnetic sensor unit;

a coil unit disposed in the magnetically shielded space and including a plurality of coils configured to apply a static magnetic field and an RF magnetic field to the magnetic sensor unit;

a $\lambda/4$ wavelength plate and a polarization beam splitter disposed to extract either one of the D1 line and the D2 line of light beams transmitted through the glass cell of the glass cell of the magnetic sensor unit; and a signal processor configured to perform lock-in detection of a detection signal of light extracted by the $\lambda/4$ wavelength plate and the polarization beam splitter, control an intensity of the static magnetic field and a frequency of the RF magnetic field generated by the coil unit according to a lock-in detection output, and obtain a measurement signal reflecting a magnetic field intensity of an object to be measured installed in the magnetically shielded space, wherein each of the first and second light source units includes:

a laser configured to output light;

an optical modulator configured to modulate the output light from the laser;

a first beam splitter disposed to split modulated light output from the optical modulator into a first light beam and a second light beam;

an intensity stabilization unit configured to control an output light intensity of the optical modulator to become a predetermined value based on the first beam of light;

a second beam splitter disposed to split the second light beam into a third light beam and a fourth light beam; and a frequency stabilization unit configured to control a cavity length of the laser corresponding to an output frequency of the laser based on a phase of light obtained from a reference glass cell that receives the third light beam, and wherein the first light source unit outputs the fourth light beam as the laser light of the D1 line subjected to intensity stabilization and frequency stabilization and the second light source unit outputs the fourth light beam as the laser light of the D2 line subjected to intensity stabilization and frequency stabilization.

6. A magnetic field measurement device comprising:

a magnetic sensor unit disposed in a magnetically shielded space, including a glass cell having alkali metal gas encapsulated therein, and configured to detect a magnetic field with use of a magneto-optical characteristic of spin-polarized alkali metal;

a first light source unit configured to generate laser light of a D1 line that is an absorption line of the alkali metal;

a second light source unit configured to generate laser light of a D2 line that is an absorption line of the alkali metal;

a half mirror disposed to introduce pump light obtained by coaxially combining the laser light of the D1 line from the first light source unit and the laser light of the D1 line from the second light source into the glass cell of the magnetic sensor unit;

a coil unit disposed in the magnetically shielded space and including a plurality of coils configured to apply a static magnetic field and an RF magnetic field to the magnetic sensor unit;

a λ/4 wavelength plate and a polarization beam splitter disposed to extract either one of the D1 line and the D2 line of light beams transmitted through the glass cell of the glass cell of the magnetic sensor unit; and a signal processor configured to perform lock-in detection of a detection signal of light extracted by the λ/4 wavelength plate and the polarization beam splitter, control an intensity of the static magnetic field and a frequency of the RF magnetic field generated by the coil unit according to a lock-in detection output, and obtain a measurement signal reflecting a magnetic field intensity of an object to be measured installed in the magnetically shielded space, wherein each of the first and second light source units includes:

a laser configured to output light;

a first beam splitter disposed to split the output light from the laser into a first light beam and a second light beam;

a frequency stabilization unit configured to generate a frequency stabilization control signal which controls a cavity length of the laser corresponding to an output frequency of the laser based on a phase of light obtained from a reference glass cell that receives the first light beam;

an optical modulator configured to modulate the second light beam;

a second beam splitter disposed to split modulated light from the optical modulator into a third light beam and a fourth light beam; and an intensity stabilization unit configured to control an output light intensity of the optical modulator to become a predetermined value based on the third light beam, and wherein the first light source unit outputs the fourth light beam as the laser light of the D1 line subjected to intensity stabilization and frequency stabilization and the second light source unit outputs the fourth light beam as the laser light of the D2 line subjected to intensity stabilization and frequency stabilization.

* * * * *